US00PP25229P2

(12) United States Plant Patent
Verwer

(10) Patent No.: US PP25,229 P2
(45) Date of Patent: Jan. 13, 2015

(54) ***DAHLIA* PLANT NAMED 'LILAC FOX'**

(50) Latin Name: *Dahlia hybrida*
Varietal Denomination: Lilac Fox

(71) Applicant: Aad W. M. Verwer, Lisse (NL)

(72) Inventor: Aad W. M. Verwer, Lisse (NL)

(73) Assignee: Verwer Dahlias BV, Lisse (NL)

( * ) Notice: Subject to any disclaimer, the term of this patent is extended or adjusted under 35 U.S.C. 154(b) by 21 days.

(21) Appl. No.: 13/815,885

(22) Filed: Mar. 15, 2013

(51) Int. Cl.
*A01H 5/00* (2006.01)

(52) U.S. Cl.
USPC ..... Plt./321

(58) Field of Classification Search
USPC ..... Plt./321
See application file for complete search history.

*Primary Examiner* — Kent L Bell
(74) *Attorney, Agent, or Firm* — C. A. Whealy

(57) ABSTRACT

A new and distinct cultivar of *Dahlia* plant named 'Lilac Fox', characterized by its upright plant habit; vigorous growth habit; high cut flower production; freely flowering habit; spherical decorative-type inflorescence form with red purple-colored ray florets held on strong and straight flower stems; and good keeping quality.

2 Drawing Sheets

Botanical designation: *Dahlia hybrida.*
Cultivar denomination: 'LILAC FOX'.

BACKGROUND OF THE INVENTION

The present invention relates to a new and distinct cultivar of *Dahlia* plant, botanically known as *Dahlia hybrida*, typically grown as a cut flower and hereinafter referred to by the name 'Lilac Fox'.

The new *Dahlia* plant is a naturally-occurring branch mutation of *Dahlia hybrida* 'Zundert Mystery Fox', not patented. The new *Dahlia* plant was discovered and selected by the Inventor on a single flowering plant within a population of plants of 'Zundert Mystery Fox' in a controlled outdoor nursery environment in Lisse, The Netherlands in 2007.

Asexual reproduction of the new *Dahlia* plant by cuttings since the spring of 2008 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Lilac Fox'. These characteristics in combination distinguish 'Lilac Fox' as a new and distinct *Dahlia* plant:

1. Upright plant habit.
2. Vigorous growth habit.
3. High cut flower production.
4. Freely flowering habit.
5. Spherical decorative-type inflorescence form with red purple-colored ray florets held on strong and straight flower stems.
6. Good keeping quality.

Plants of the new *Dahlia* differ primarily from plants of the parent, 'Zundert Mystery Fox' primarily in ray floret color as plants of 'Zundert Mystery Fox' has salmon orange-colored ray florets.

Plants of the new *Dahlia* can be compared to plants of the *Dahlia hybrida* 'Karma Lagoon', disclosed in U.S. Plant Pat. No. 11,346. In side-by-side comparisons conducted in Lisse, The Netherlands, plants of the new *Dahlia* differed from plants of 'Karma Lagoon' in the following characteristics:

1. Plants of the new *Dahlia* produced more flowering stems than plants of 'Karma Lagoon'.
2. Plants of the new *Dahlia* had green-colored leaves whereas plants of 'Karma Lagoon' had leaves that tended to bronze.
3. Inflorescences of plants of the new *Dahlia* were more spherical than inflorescences of plants of 'Karma Lagoon'.
4. Plants of the new *Dahlia* and 'Karma Lagoon' differed in ray floret color as plants of 'Karma Lagoon' had purple violet-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of typical flowering plants of 'Lilac Fox' grown in an outdoor nursery.

The photograph on the second sheet is a close-up view of a typical flowering plant of 'Lilac Fox'.

DETAILED BOTANICAL DESCRIPTION

The photographs and following observations and measurements describe plants grown during the summer and autumn in ground beds in an outdoor nursery in Lisse, The Netherlands and under cultural practices typical of commercial *Dahlia* production. During the production of the plants, day temperatures ranged from 10° C. to 25° C. and night temperatures ranged from 8° C. to 20° C. Plants were pinched one time about three weeks after planting. Plants were 14 weeks old when the photographs and description were taken. In the following description, color references are made to The Royal Horticultural Society Colour Chart, 1995 Edition, except where general terms of ordinary dictionary significance are used.

Botanical classification: *Dahlia hybrida* 'Lilac Fox'.

Parentage: Naturally-occurring branch mutation of *Dahlia hybrida* 'Zundert Mystery Fox', not patented.

Propagation:

*Type*.—By vegetative cuttings.

*Time to initiate roots, summer*.—About ten days at soil temperatures of 15° C.

*Time to initiate roots, winter*.—About 12 to 14 days at soil temperatures of 15° C.

*Time to produce a rooted young plant, summer*.—About 21 days at soil temperatures of 15° C.

*Time to produce a rooted young plant, winter*.—About 25 days at soil temperatures of 15° C.

*Root description*.—Fine, fleshy; white in color.

*Rooting habit*.—Freely branching; dense.

*Tubers*.—Length: About 18 cm. Diameter: About 15 cm. Texture: Corky. Color: Close to 159B.

Plant description:

*Plant and growth habit*.—Upright plant habit; inverted triangular plant form; freely basal branching with about six lateral branches per plant; about 16 flowering stems are produced per year; inflorescences held above the foliar plane on strong and straight peduncles; vigorous growth habit.

*Plant height*.—About 70 cm.

*Plant diameter or spread*.—About 30 cm to 35 cm.

*Lateral branches*.—Length: About 45 cm to 60 cm. Diameter: About 7 mm. Internode length: About 3 cm to 11 cm. Texture: Smooth, glabrous. Strength: Strong, straight. Color: Close to 146A.

Leaf description:

*Arrangement*.—Opposite, single or compound with three or five leaflets.

*Leaf length*.—About 12 cm to 18 cm.

*Leaf width*.—About 6 cm to 15 cm.

*Shape*.—Ovate.

*Apex*.—Acuminate.

*Base*.—Attenuate.

*Margin*.—Serrate; sinuses divergent.

*Venation pattern*.—Pinnate.

*Texture, upper and lower surfaces*.—Smooth, glabrous.

*Color*.—Developing and fully expanded leaves, upper surface: Close to 137A; venation, close to 152A. Developing and fully expanded leaves, lower surface: Close to 191A; venation, close to 145A.

*Petioles*.—Length, all leaves and leaflets: About 4.4 cm. Diameter, all leaves and leaflets: About 6 mm. Texture, upper and lower surfaces: Smooth, glabrous. Color, upper surface: Close to 152D. Color, lower surface: Close to 145A.

Inflorescence description:

*Appearance and flowering habit*.—Spherical decorative-type inflorescences with ray and disc florets developing acropetally on a receptacle; inflorescences positioned above and beyond the foliar plane on strong peduncles; inflorescences face mostly upright; freely flowering habit with typically more than 45 to 50 inflorescences developing per plant.

*Fragrance*.—None detected.

*Time to flower*.—Plants begin flowering about 70 days after planting; flower continuously during the summer and autumn in The Netherlands.

*Post-production longevity*.—Good postproduction longevity; inflorescences maintain good substance for about 20 days on the plant and for about eight days as a cut flower; inflorescences persistent.

*Inflorescence buds*.—Height: About 1.1 cm. Diameter: About 1.9 cm. Shape: Oblate. Color: Close to 72B; towards the apex and base, close to 144B.

*Inflorescence diameter*.—About 9 cm.

*Inflorescence depth* (*height*).—About 6.5 cm.

*Disc diameter*.—About 4 mm, inconspicuous.

*Receptacle height*.—About 6 mm.

*Receptacle diameter*.—About 1.2 cm.

*Receptacle color*.—Close to 145A.

*Ray florets*.—Length: About 3.6 cm. Width: About 2.1 cm. Shape: Ovate, incurved. Apex: Obtuse. Base: Attenuate. Margin: Entire. Aspect: Initially upright to horizontal to eventually recurving forming a ball-shaped inflorescence. Texture, upper and lower surfaces: Smooth, glabrous; velvety. Number of ray florets per inflorescence: About 144 arranged in about 16 whorls. Color: When opening and fully opened, upper surface: Close to 74A; mid-section, close to 74C; at the base, close to 20A. When opening and fully expanded, lower surface: Close to 74B; mid-section, close to 75B; at the base, close to 76D.

*Disc florets*.—Shape: Tubular; apex dentate. Length: About 7 mm. Diameter: About 1.8 mm. Number of disc florets per inflorescence: About 35. Color, immature: Apex: Close to 21A. Mid-section: Close to 3A. Base: Close to 2D. Color, mature: Apex: Close to 21A. Mid-section: Close to 3B. Base: Close to 21A.

*Phyllaries*.—Quantity per inflorescence: About eight arranged in a single whorl. Length: About 1.8 cm. Width: About 1 cm. Shape: Ovate. Apex: Acuminate. Base: Attenuate. Margin: Entire. Texture, upper and lower surfaces: Smooth, glabrous. Color, upper and lower surfaces: Close to 146A.

*Peduncles*.—Length, terminal peduncle: About 21 cm. Length, fourth peduncle: About 17 cm. Length, seventh peduncle: About 16 cm. Diameter: About 3 mm. Strength: Strong. Aspect: Mostly erect, straight. Texture: Smooth, glabrous. Color: Close to 165A; towards the base, close to 144B.

*Reproductive organs*.—Androecium, present on disc florets only: Quantity per disc floret: Five. Filament length: About 7 mm. Filament color: Close to 1B. Anther shape: Lanceolate. Anther length: About 4 mm. Anther color: Close to 21B. Pollen amount: Scarce. Pollen color: Close to 21A. Gynoecium, present on ray and disc florets: Quantity per floret: One. Pistil length: About 3 mm. Stigma shape: Lanceolate. Stigma color: Close to 2B. Style length: About 1.1 mm. Style color: Close to 4D. Ovary color: Close to 4C. Fruits and seeds: Fruit and seed development has not been observed on plants of the new *Dahlia*.

Disease & pest resistance: Plants of the new *Dahlia* have not been shown to be resistant to pathogens and pests common to *Dahlia* plants.

Temperature tolerance: Plants of the new *Dahlia* have been observed to tolerate temperatures from about 0° C. to about 35° C.

It is claimed:

1. A new and distinct *Dahlia* plant named 'Lilac Fox' as illustrated and described.

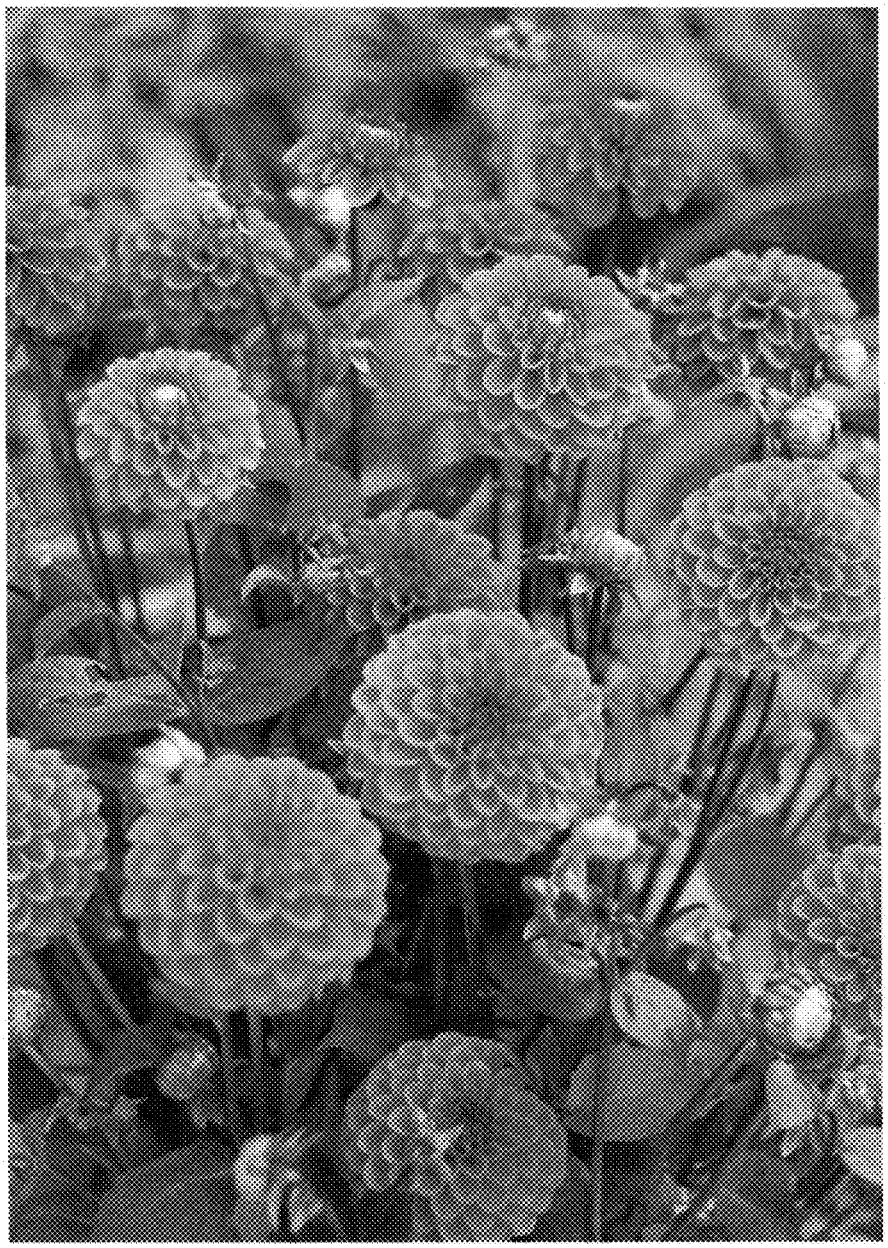

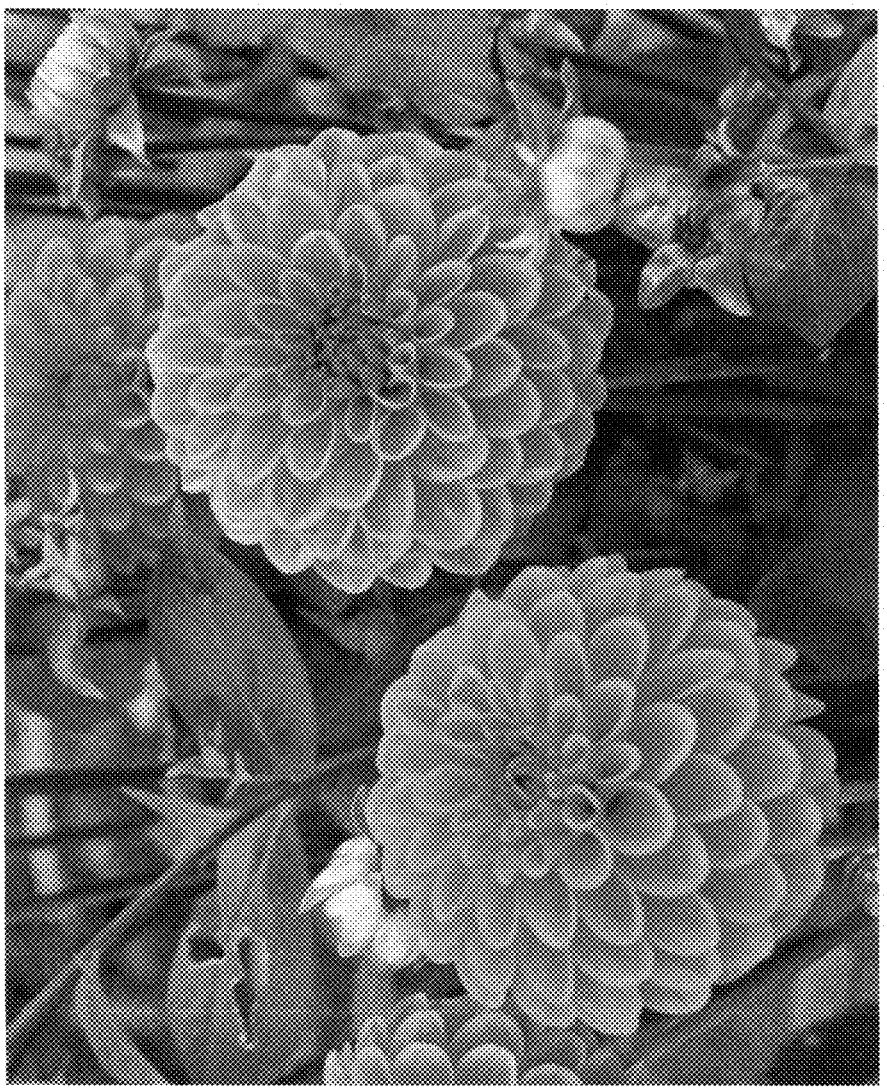

* * * * *